United States Patent
Dagsland et al.

(10) Patent No.: US 6,484,717 B1
(45) Date of Patent: Nov. 26, 2002

(54) INHALATION DEVICE

(75) Inventors: Allan Dagsland, Karlshamn (SE); Risto Virtanen, Nurmijärvi (FI)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/068,385

(22) Filed: May 8, 1998

Related U.S. Application Data

(63) Continuation of application No. PCT/SE98/00458, filed on Mar. 13, 1998.

(30) Foreign Application Priority Data

Mar. 14, 1997 (SE) ................................................ 9700938

(51) Int. Cl.⁷ ........................ A61M 15/00; A61M 16/00
(52) U.S. Cl. ............................... 128/203.15; 128/203.12
(58) Field of Search ........................ 128/203.12, 203.15; 222/636; 604/58

(56) References Cited

U.S. PATENT DOCUMENTS

| | | | |
|---|---|---|---|
| 4,668,218 A | | 5/1987 | Virtanen |
| 4,805,811 A | * | 2/1989 | Wetterlin .................... 222/337 |
| 4,907,583 A | * | 3/1990 | Wetterlin et al. ....... 128/203.15 |
| 5,174,473 A | * | 12/1992 | Marelli ......................... 222/38 |
| 5,331,953 A | * | 7/1994 | Andersson et al. .... 128/200.14 |
| 5,394,868 A | * | 3/1995 | Ambrosio et al. ..... 128/203.15 |
| 5,505,195 A | * | 4/1996 | Wolf et al. ............. 128/203.15 |
| 5,505,196 A | * | 4/1996 | Herold et al. .......... 128/203.15 |
| 5,549,101 A | * | 8/1996 | Trofast et al. .......... 128/203.15 |
| 5,575,280 A | * | 11/1996 | Gupte et al. ............ 128/203.15 |
| 5,634,900 A | * | 6/1997 | Makino et al. ................ 604/58 |
| 5,687,710 A | * | 11/1997 | Ambrosio et al. ..... 128/203.15 |
| 5,699,789 A | * | 12/1997 | Hendricks ............... 128/203.15 |
| 5,740,792 A | * | 4/1998 | Ashley et al. .......... 128/203.15 |
| 5,829,434 A | * | 11/1998 | Ambrosio et al. ..... 128/203.15 |
| 5,839,429 A | * | 11/1998 | Marnfeldt et al. ..... 128/200.14 |
| 6,076,521 A | * | 6/2000 | Lindahl et al. ......... 128/203.15 |
| 6,095,136 A | * | 8/2000 | Virtanen ................. 128/203.15 |
| 6,142,145 A | * | 11/2000 | Dagsland et al. ...... 128/203.15 |
| 6,182,655 B1 | * | 2/2001 | Keller et al. ........... 128/203.15 |
| 6,240,918 B1 | * | 6/2001 | Ambrosio et al. ..... 128/203.15 |
| 6,257,232 B1 | * | 7/2001 | Andersson et al. .... 128/203.15 |
| 6,325,061 B1 | * | 12/2001 | Dagsland ............... 128/203.15 |

FOREIGN PATENT DOCUMENTS

| | | |
|---|---|---|
| EP | 0 237 507 A1 | 9/1987 |
| TW | 236569 | 12/1994 |
| WO | WO 86/05991 | 10/1986 |
| WO | WO 92/00771 | 1/1992 |
| WO | WO94/14492 | 7/1994 |
| WO | WO95/11715 | 5/1995 |

OTHER PUBLICATIONS

Copy of PCT International Search Report PCT/SE98/00458.

* cited by examiner

*Primary Examiner*—Aaron J. Lewis
(74) *Attorney, Agent, or Firm*—Fish & Richardson P.C.

(57) ABSTRACT

An inhaler for administering powder by inhalation and a method of constructing the same. The inhaler includes an inhaler body having an opening therein and an indicating wheel disposed in the inhaler body for providing an indication as to the usage of the inhaler. The indicating wheel is disposed such that at least part thereof is visible through the opening and so as to be rotatable in a diametrical plane containing a central axis of the inhaler body. The inhaler also includes a divider substantially closing one end of the inhaler body and a storage unit disposed in the inhaler body. The storage unit includes a storage chamber for storing powder for inhalation. The inhaler body and the divider are formed as a single integral unit of an opaque material and the storage unit is formed of a transparent material and has a portion which substantially fills the opening.

10 Claims, 8 Drawing Sheets

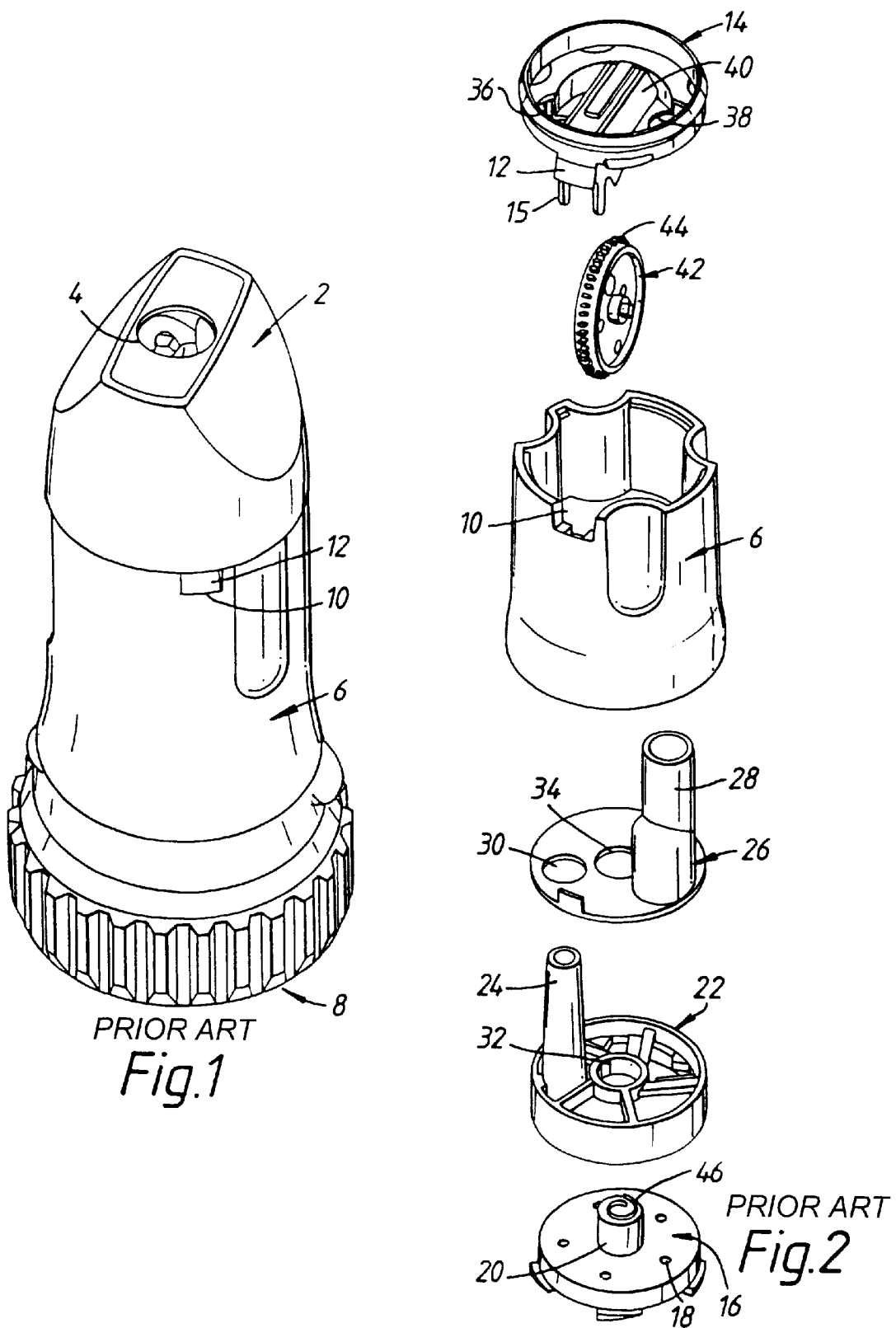

INHALATION DEVICE

This application is a continuation of PCT/SE98/00458 filed Mar. 13, 1998.

BACKGROUND

The present invention relates to a powder inhaler and a method of constructing the same. More particularly, the present invention relates to a powder inhaler having a reduced number of component parts as compared to known powder inhalers, which powder inhaler is hence easier to construct than known powder inhalers.

A number of powder inhalers are known which use different systems for introducing a dose of powder into an air stream. Typically, the powder is inhaled into the lungs of a patient in order to treat, for example, asthma.

FIG. 1 illustrates such a powder inhaler. The inhaler comprises a mouthpiece 2 comprising an air chamber (not illustrated) and an outlet nozzle 4, an inhaler body 6 and a rotatable grip portion 8 for operating a dosing mechanism for providing doses of powder for inhalation. The inhaler body 6 is provided with an opening 10 which is filled with a window 12 through which an indicating wheel 42 is visible so as to provide an indication as to the usage of the inhaler.

FIG. 2 illustrates in exploded view component parts disposed within and to the inhaler body 6. The inhaler body 6 is capped with a divider 14 which is fixed thereto and separates the air chamber in the mouthpiece 2 from a major part of the inhaler body 6. For aesthetic reasons the inhaler body 6 is an opaque moulding. The divider 14 is a transparent moulding which has a depending tongue 15, a part of which forms the window 12.) When the inhaler is assembled, the only part of the divider 14 which is visible is the part of the tongue 15 forming the window 12, and thus the overall appearance of the inhaler is unaffected.

Within the inhaler body 6 are housed the component parts of the dosing mechanism. These component parts include a dosing unit 16 which comprises a plurality of dosing means 18 and has a central axial shaft 20, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft through central openings 32, 34 in the inhalation unit 22 and the storage unit 26 respectively. When so assembled, the upper ends of the inhalation channel 24 and the storage chamber 28 pass respectively through first and second openings 36, 38 in the divider 14.

In use, powder is transferred from the storage chamber 28 to one of the dosing means 18, and, with rotation of the dosing unit 16, the one dosing means 18 provides a dose of powder to the inhalation channel 24. On inhalation by a user the powder is drawn up through the air chamber and out of the outlet nozzle 4 of the mouthpiece 2.

As illustrated in FIGS. 2 and 3, the divider 14 further comprises supporting means 40 for rotatably supporting an indicating wheel 42. The indicating wheel 42 has a plurality of teeth 44 disposed around the periphery thereof which engage with a spiral groove or protrusion 46 on the end face of the shaft 20 of the dosing unit 16. The supporting means 40 is configured to align the indicating wheel 42 such that a part of the periphery thereof is disposed adjacent the inner surface of the window 12.

In use, as the dosing unit 16 is rotated, the spiral groove or protrusion 46 engages with one or more of the teeth 44 on the indicating wheel 42 so as to rotate the same. In this way, by providing a coloured marking on the periphery of the indicating wheel 42, it is possible to provide the user with a visible indication at the window 12 as to the usage of the inhaler.

Although the above-described known powder inhaler functions quite adequately, its construction is relatively complicated and it is formed from a large number of component parts. It is thus an aim of the present invention to provide a powder inhaler which has a fewer number of component parts and is of simpler construction.

SUMMARY OF THE INVENTION

Accordingly, the present invention provides an inhaler for administering powder by inhalation, comprising: an inhaler body having an opening therein; an indicating wheel disposed in the inhaler body for providing an indication as to the usage of the inhaler, the indicating wheel being disposed such that at least part thereof is visible through the opening and so as to be rotatable in a diametrical plane containing the central axis of the inhaler body; a divider substantially closing one end of the inhaler body; and a storage unit disposed in the inhaler body, the storage unit comprising a storage chamber for storing powder for inhalation; wherein that the inhaler body and the divider are formed as a single integral unit of an opaque material and in that the storage unit is formed of a transparent material and has a portion which substantially fills the opening.

Embodiments of this aspect of the invention may include one or more of the following features.

Preferably, the inhaler further comprises an inhalation unit disposed in the inhaler body, the inhalation unit having an inhalation channel through which powder is in use inhaled. In a preferred embodiment the inhalation unit and the storage unit are formed as a single integral unit.

Preferably, the inhaler further comprises a dosing unit disposed in the inhaler body so as to be rotatable about the central axis thereof for introducing a dose of powder into the inhalation channel, the dosing unit having a central shaft co-axial with the central axis of the inhaler body, the central shaft having an end face with a spiral groove or protrusion and the indicating wheel having a toothed periphery for engaging the spiral groove or protrusion.

In a preferred embodiment the indicating wheel is rotatably supported by the storage unit and the divider is constructed as a substantially flat member so as to minimize the risk of powder accumulting on the upper surface thereof.

Preferably, the inhaler body further comprises an air inlet in a side wall thereof, the air inlet allowing air to be drawn to the dosing unit and through the inhalation channel. In a preferred embodiment the air inlet is provided in a recess in the inhaler body.

In another aspect, the invention provides a method of constructing an inhaler for administering powder by inhalation, comprising the steps of: providing as a single integral unit of an opaque material an inhaler body with a divider substantially closing one end thereof; fitting an indicating wheel in the inhaler body in such a manner as to be rotatable in a diametrical plane containing the central axis thereof, the inhaler body having an opening through which at least part of the indicating wheel is visible and the indicating wheel providing an indication as to the usage of the inhaler; and fitting a storage unit comprising a storage chamber for storing powder for inhalation in the inhaler body, the storage unit being formed of a transparent material and including a portion which substantially fills the opening.

Medicaments suitable for administration by the powder inhaler of the present invention are any which may be delivered by inhalation and include for example β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompany drawings.

BRIEF DESCRIPTION OF THE DRAWINGS

FIG. 1 illustrates a perspective view of a known powder inhaler;

FIG. 2 illustrates in exploded view component parts of the inhaler of FIG. 1;

DETAILED DESCRIPTION OF THE PREFERRED EMBODIMENTS

Structurally, the powder inhalers in accordance with the preferred embodiments of the present invention have many features in common with the above-described known powder inhaler. For this reason, and in order to avoid unnecessary duplication of description, only the structural differences will be described in detail and reference is made to the preceding description of the known powder inhaler.

Figure 3:
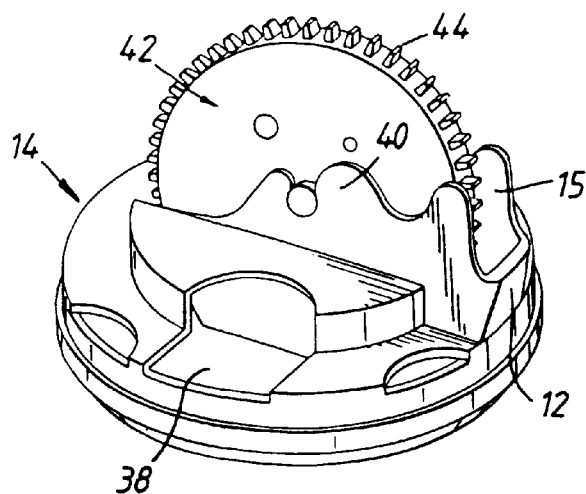
FIG. 3 illustrates component parts of the inhaler of FIG. 1.
Figure 4:
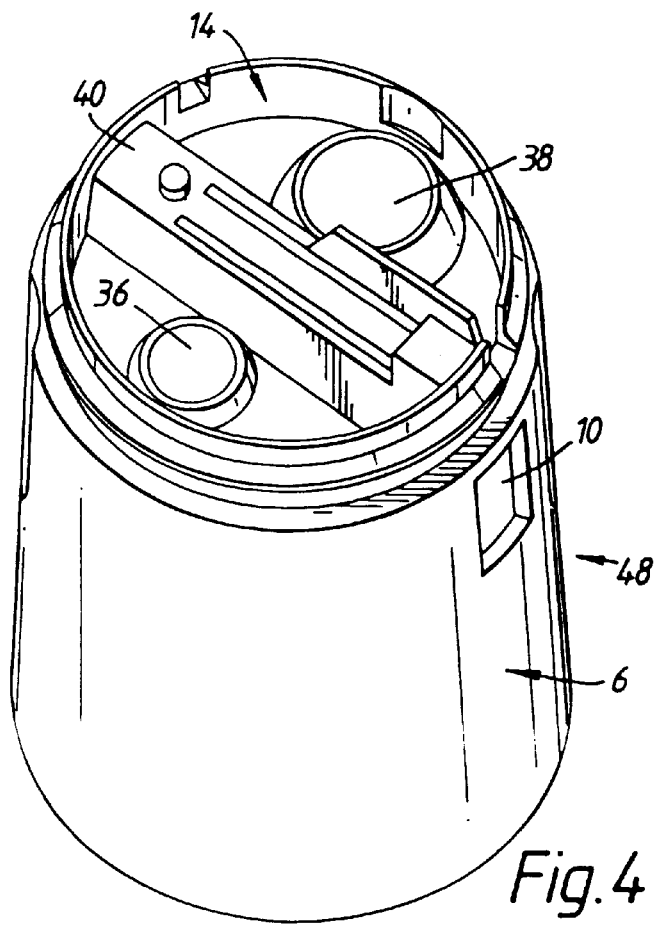
FIGS. 4 and 5 illustrate component parts of a powder inhaler in accordance with a first embodiment of the present invention.
Figure 5:
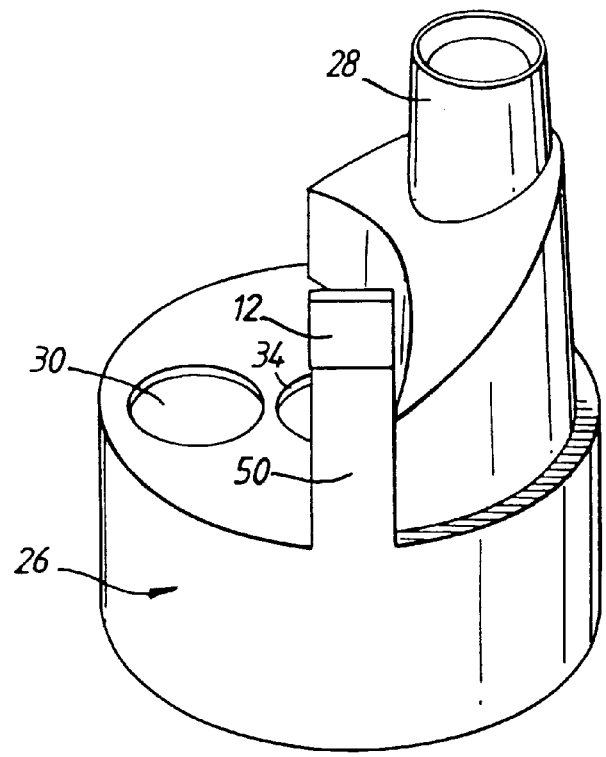

FIGS. 4 and 5 illustrate respectively a body part 48 and a storage unit 26 of a powder inhaler in accordance with a first embodiment of the present invention.

This inhaler is a modification of the above-described known powder inhaler. This inhaler differs from the above-described known powder inhaler in comprising a body part 48 which is a single part moulded from an opaque material that comprises both the inhaler body 6 and the divider 14. As in the above-described known powder inhaler, the inhaler body 6 includes the opening 10 through which the indicating wheel 42 is visible. This inhaler further differs from the above-described known powder inhaler in that the storage unit 26 is formed from a transparent material and comprises a tongue 50, one part, in this embodiment the distal end, of which is shaped and dimensioned such that when the storage unit 26 is fitted in the inhaler body 6 that part of the tongue 50 fills the opening 10 so as to provide the window 12. As in the above-described known powder inhaler, the indicating wheel 42 is rotatably supported to the underside of the divider 14 such that at least a part of the periphery of the indicating wheel 42 is visible through the window 12. In a preferred embodiment one or both of the inhalation unit 22 and the storage unit 26 are formed together with the inhaler body 6 as a single integral unit.

Figure 6:
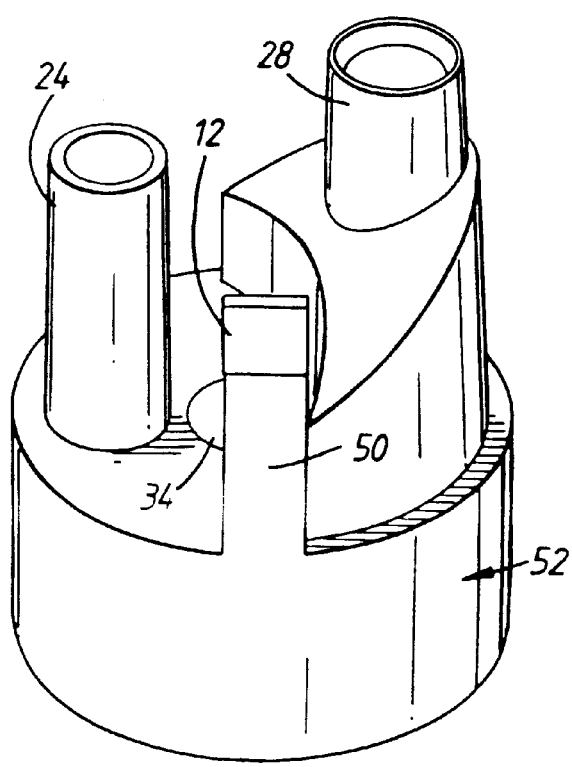
FIG. 6 illustrates a component part of a powder inhaler in accordance with a second embodiment of the present invention.

FIG. 6 illustrates a structural unit 52 of a powder inhaler in accordance with a second embodiment of the present invention.

This inhaler is a modification of the inhaler of the above-described first embodiment. This inhaler differs from the inhaler of the above-described first embodiment in that the inhalation unit 22 and the storage unit 26 are replaced by a structural unit 52 which is a single part moulded from a transparent material. The structural unit 52 comprises the tongue 50, a part of which fills the opening 10 so as to provide the window 12. Again, as in the inhaler of the above-described first embodiment, the indicating wheel 42 is rotatably mounted to the underside of the divider 14.

Figure 7:
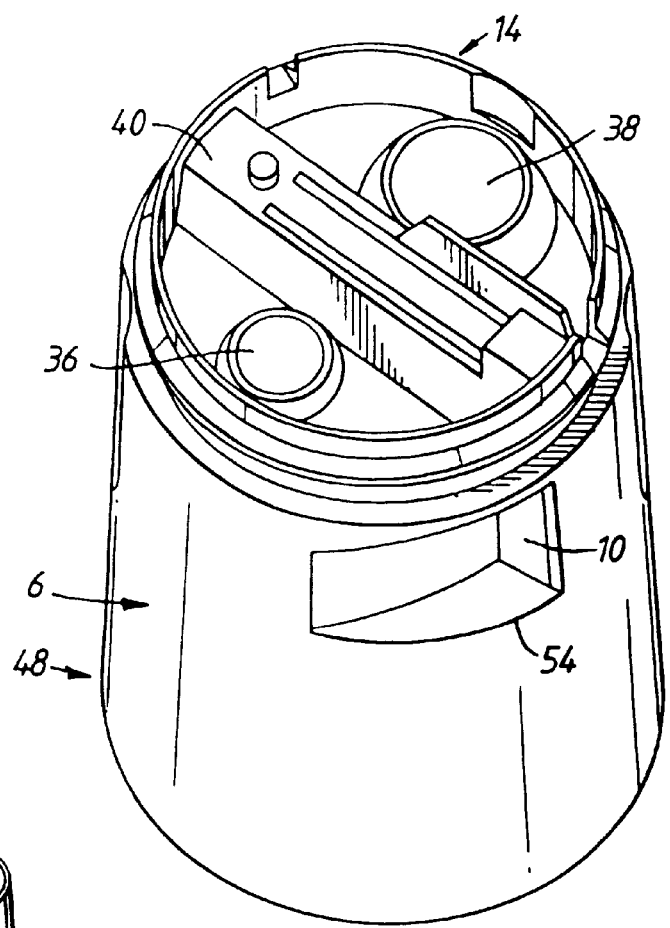
FIGS. 7 and 8 illustrate component parts of a powder inhaler in accordance with a third embodiment of the present invention.
Figure 8:
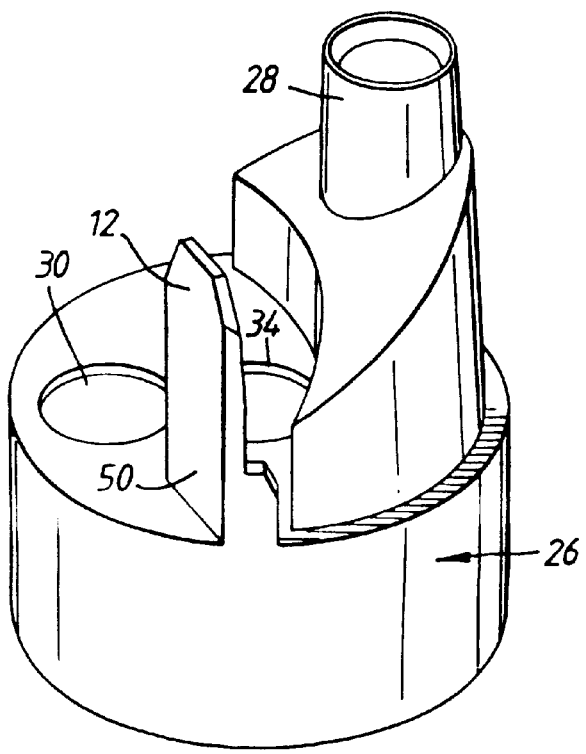

FIGS. 7 and 8 illustrate respectively a body part 48 and a storage unit 26 of a powder inhaler in accordance with a third embodiment of the present invention.

This inhaler is a modification of the inhaler of the above-described first embodiment. In this embodiment the body part 48 differs in that the peripheral wall of the inhaler body 6 includes a recess 54 in a side of which is provided the opening 10 and the storage unit 26 differs in that the tongue 50 is oriented substantially radially so as to align with the opening 10 in the recess 54.

Figure 9:
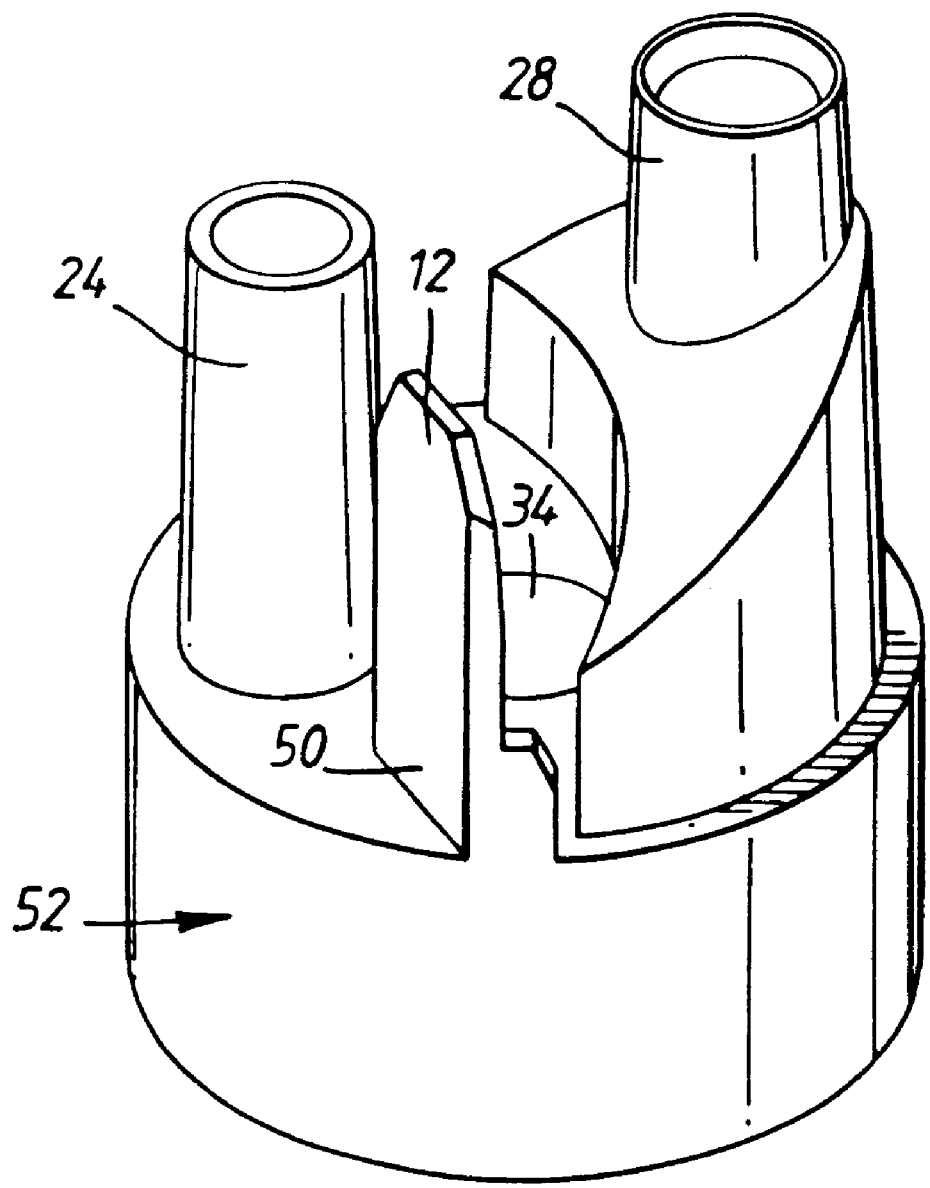
FIG. 9 illustrates a component part of a powder inhaler in accordance with a fourth embodiment of the present invention.

FIG. 9 illustrates a structural unit 52 of a powder inhaler in accordance with a fourth embodiment of the present invention.

This inhaler is a modification of the inhaler of the above-described third embodiment. In this embodiment the inhalation unit 22 and the storage unit 26 of the inhaler of the above-described third embodiment are replaced by a structural unit 52 which is a single part moulded from a transparent material.

Figure 10:
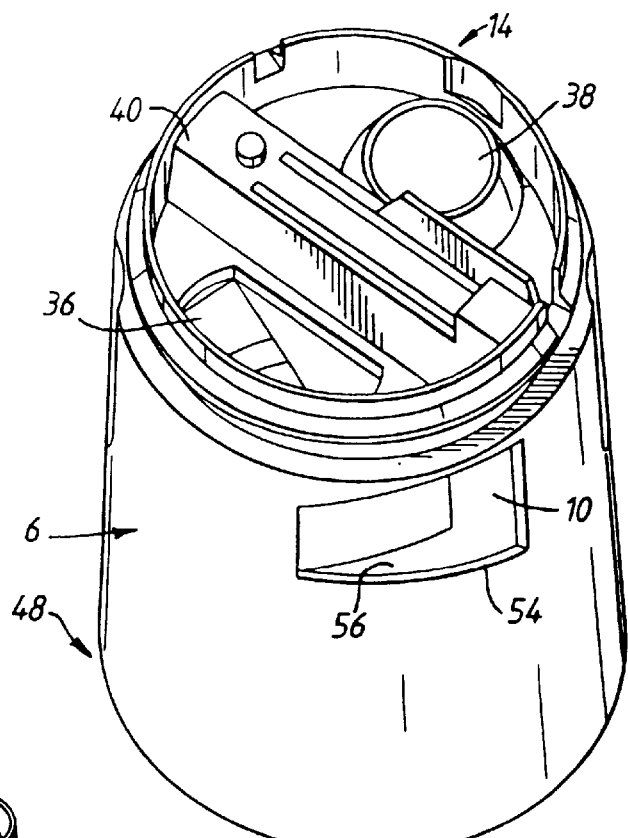
FIGS. 10 and 11 illustrate component parts of a powder inhaler in accordance with a fifth embodiment of the present invention.
Figure 11:
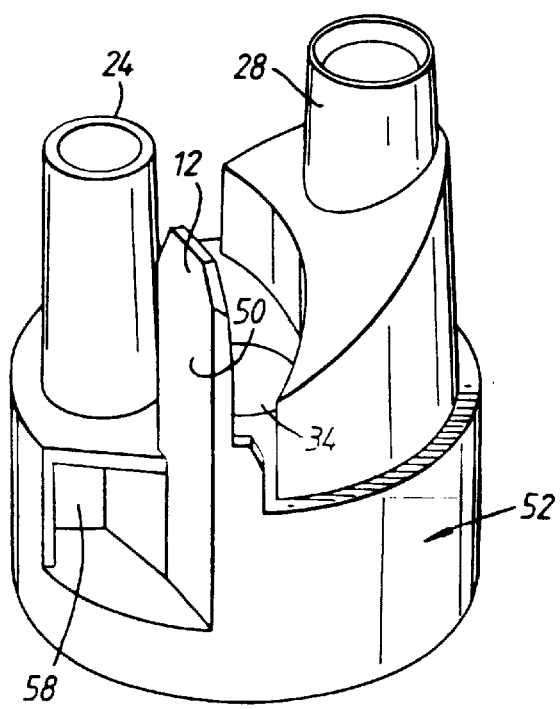

FIGS. 10 and 11 illustrate respectively a body part 48 and a structural unit 52 of a powder inhaler in accordance with a fifth embodiment of the present invention.

This inhaler is a modification of the inhaler of the above-described fourth embodiment. In this embodiment the body part 48 differs in that a lower section of the recess 54 in the inhaler body 6 is cut away to provide an opening 56 into the inhaler body 6 and the is structural unit 52 differs in that the lower end of the inhalation channel 24 is provided with a lateral opening 58. During inhalation by a user, air is drawn through the opening 56 in the recess 54 and then the lateral opening 58 in the inhalation channel 24 where a dose of powder is entrained, which powder is then drawn up the inhalation channel 24 into and through the air chamber and out of the outlet nozzle 4 of the mouthpiece 2.

Figure 12:
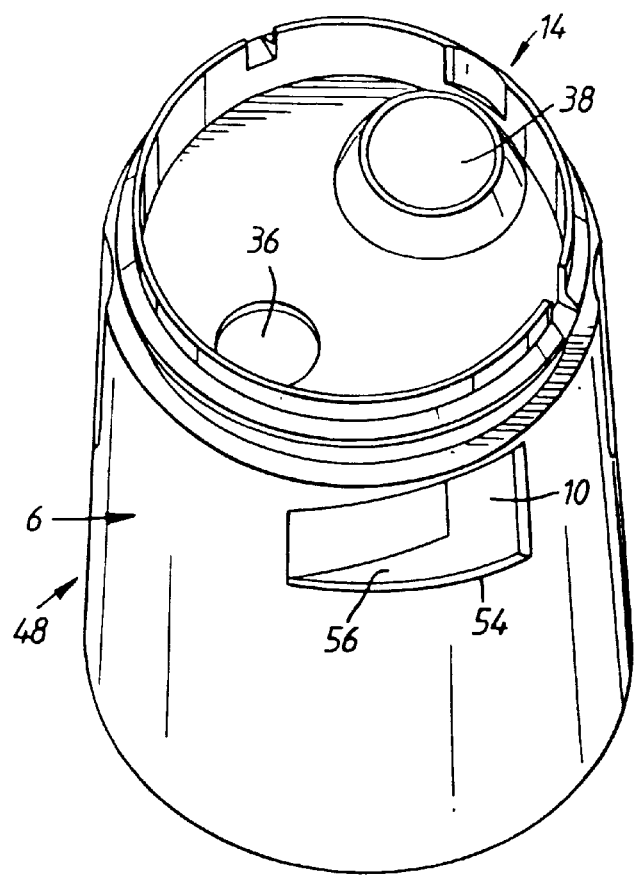
FIGS. 12 and 13 illustrate component parts of a powder inhaler in accordance with a sixth embodiment of the present invention.
Figure 13:
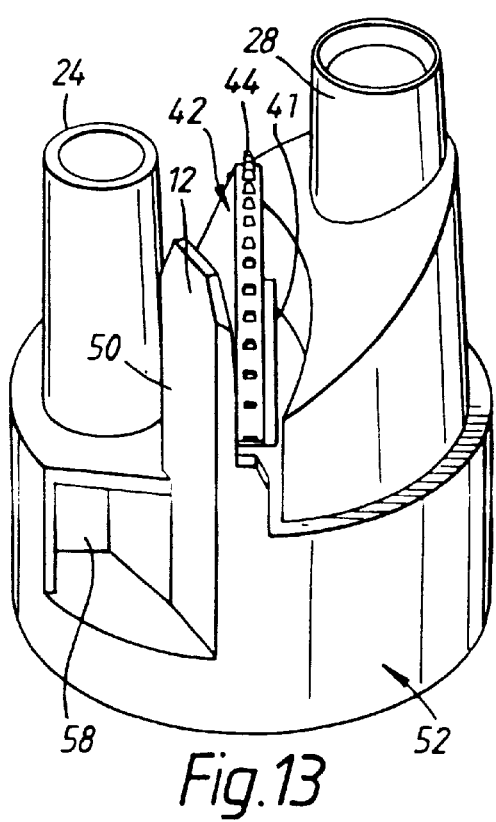

FIGS. 12 and 13 illustrate respectively a body part 48 and a structural unit 52 of a powder inhaler in accordance with a sixth embodiment of the present invention.

This inhaler is a modification of the inhaler of the above-described fifth embodiment. This inhaler differs form the inhaler of the above-described fifth embodiment in that the structural unit 52 includes the supporting means 41 for rotatably supporting the indicating wheel 42 instead of the divider 14 and in that the divider 14 is formed with a substantially flat top surface. In this way, the risk of powder accumulating at this top surface is minimized. This is of particular importance where the top surface of the divider 14 forms the lower wall of the air chamber of the mouthpiece 2.

Figure 14:
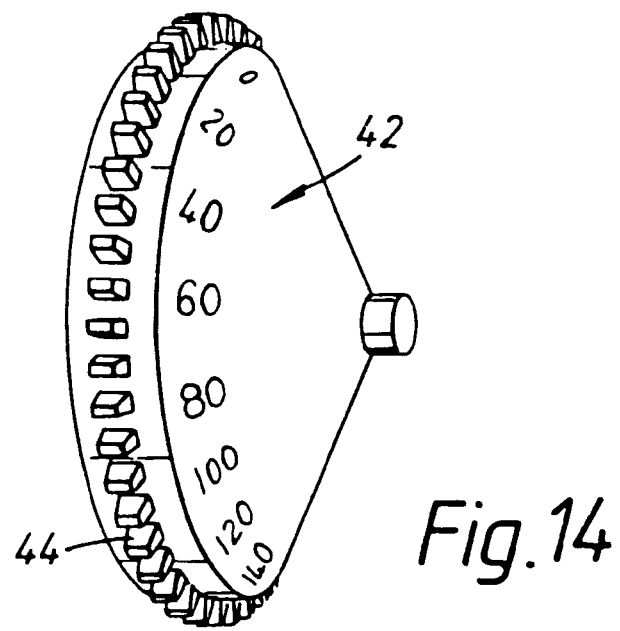
FIGS. 14 and 15 illustrate indicating wheels for use with the powder inhalers of any of FIGS. 7 to 13.
Figure 15:
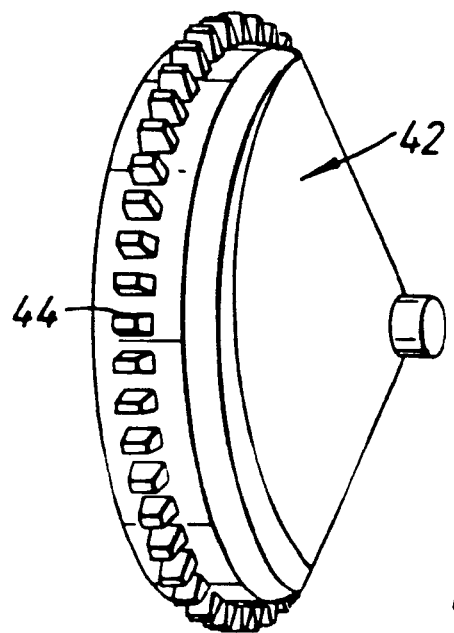

In any of the inhalers of the above-described third to sixth embodiments the indicating wheel 42 may be disposed such that a side surface thereof is visible through the opening 10 in the recess 54 in the inhaler body 6. In order to improve visibility, one of the side surfaces of the indicating wheel 42 can be formed as a conical surface, with the surface of the cone enclosing an angle of from 10° to 30°, preferably about 15°, with the rotational plane of the indicating wheel 42. The indicating wheel 42 may have indications on the surface of the cone, for instance numeric indications of increasing or decreasing value, for indicating the number of times the inhaler has been operated or the number of times it may still be operated. Alternatively, or additionally, the indicating wheel 42 may have a circumferential band of changing width along its length, such that the width visible through the window 12 is representative of the number of doses delivered. Suitable indicating wheels are illustrated in FIGS. 14 and 15. Colour changes may also be used to indicate the number of doses delivered. Such colour changes may also be applied in conjunction with the indications described hereinabove. For instance, by using numerals of different colour, or by using a band, the colour of which changes along its length.

In each of the above-described embodiments the storage chamber 28 is crescent-shaped in plan view and thereby provides an increased storage capacity. It will be understood, however, that the storage chamber 28 may be formed as a cylinder as in the above-described known powder inhaler.

Finally, it will be understood by a person skilled in the art that the present invention is not limited to the described embodiments but can be modified in many different ways within the scope of the appended claims.

What is claimed is:

1. An inhaler for administering powder by inhalation, comprising:
    an inhaler body provided with a window;
    a divider substantially closing one end of the inhaler body and being integrally formed therewith as a single seamless/contiguous integral unit;
    an indicating wheel disposed in the inhaler body for providing an indication as to the usage of the inhaler, the indicating wheel being disposed such that at least part thereof is visible through the window and so as to be rotatable in a diametrical plane containing a central axis of the inhaler body; and
    a storage unit disposed in the inhaler body, the storage unit comprising a storage chamber for storing powder for inhalation;
    wherein the inhaler body includes an opening through which at least part of the indicating wheel is visible, the inhaler body and the divider are formed of an opaque material, and the storage unit is formed of a transparent material and includes a portion which substantially fills the opening and provides the window.

2. The inhaler according to claim 1, further comprising an inhalation unit disposed in the inhaler body, the inhalation unit comprising an inhalation channel through which powder is in use inhaled.

3. The inhaler according to claim 2, wherein the inhalation unit and the storage unit are formed as a single seamless/contiguous integral unit.

4. The inhaler according to claim 2, further comprising a dosing unit disposed in the inhaler body so as to be rotatable about the central axis thereof for introducing a dose of powder to the inhalation channel, wherein the dosing unit has a central shaft co-axial with the central axis of the inhaler body, the central shaft having an end face with a spiral groove or protrusion and the indicating wheel having a toothed periphery for engaging the spiral groove or protrusion.

5. The inhaler according to claim 3, wherein said seamless/contiguous integral unit further comprises supporting means for rotatably supporting the indicating wheel.

6. The inhaler according to claim 1, wherein the storage chamber has an arcuate cross section.

7. The inhaler according to claim 4, wherein the inhaler body further comprises an air inlet in a side wall thereof, the air inlet allowing air to be drawn to the dosing unit and through the inhalation channel.

8. The inhaler according to claim 1, wherein the inhaler body is substantially cylindrical.

9. A method of constructing an inhaler for administering powder by inhalation, comprising the steps of:
    providing as a single seamless/contiguous integral unit of an opaque material an inhaler body with a divider substantially closing one end thereof;
    fitting an indicating wheel in the inhaler body in such a manner as to be rotable in a diametrical plane containing a central axis thereof, the inhaler body having an opening through which at least part of the indicating wheel is visible and the indicating wheel providing an indication as to the usage of the inhaler; and
    fitting a storage unit comprising a storage chamber for storing powder for inhalation in the inhaler body, the storage unit being formed of a transparent material and including a portion which substantially fills the opening.

10. An inhaler for administering powder by inhalation, comprising:
    an inhaler body provided with a window;
    a divider substantially closing one end of the inhaler body and being integrally formed therewith as a single seamless/contiguous integral unit;
    an indicating wheel disposed in the inhaler body for providing an indication as to the usage of the inhaler, the indicating wheel being disposed such that at least part thereof is visible through the window and so as to be rotatable in a diametrical plane containing a central axis of the inhaler body; and a storage unit disposed in the inhaler body, the storage unit comprising a storage chamber for storing powder for inhalation;

wherein the inhaler body includes an opening through which at least a part of the indicating wheel is visible, the inhaler body and the divider are formed of an opaque material, and the storage unit includes an extension portion formed of a transparent material that extends to the opening and substantially fills the opening to provide the window.

* * * * *